United States Patent
Bhaggan et al.

(10) Patent No.: US 7,910,757 B2
(45) Date of Patent: Mar. 22, 2011

(54) PROCESS FOR THE PREPARATION OF FATTY ACIDS

(75) Inventors: Krishnadath Bhaggan, Wormerveer (NL); Genwang Zhang, Anqing (CN); Zheng Guo, Anqing (CN); Shuhong Cheng, Anqing (CN); Youchun Yan, Wormerveer (NL); Erik Schweitzer, Wormerveer (NL)

(73) Assignees: Lipid Nutrition B.V., Wormerveer (NL); Anqing Zhongchuang Bioengineering Co., Ltd., Anqing (CN)

( * ) Notice: Subject to any disclaimer, the term of this patent is extended or adjusted under 35 U.S.C. 154(b) by 595 days.

(21) Appl. No.: 11/883,642

(22) PCT Filed: Feb. 2, 2006

(86) PCT No.: PCT/EP2006/001020
§ 371 (c)(1),
(2), (4) Date: Jun. 4, 2008

(87) PCT Pub. No.: WO2006/082093
PCT Pub. Date: Aug. 10, 2006

(65) Prior Publication Data
US 2009/0042985 A1    Feb. 12, 2009

(30) Foreign Application Priority Data

Feb. 4, 2005  (CN) .......................... 2005 1 0054223
Feb. 14, 2005  (EP) ..................................... 05250836

(51) Int. Cl.
*C07B 35/08*    (2006.01)
(52) U.S. Cl. ...................................... 554/126
(58) Field of Classification Search ................... 554/126
See application file for complete search history.

(56) References Cited

U.S. PATENT DOCUMENTS

| | | | |
|---|---|---|---|
| 4,792,418 A | 12/1988 | Rubin et al. | |
| 6,395,778 B1 | 5/2002 | Luthria | 514/549 |
| 6,479,683 B1 | 11/2002 | Abney et al. | |
| 2002/0169332 A1* | 11/2002 | Saebo et al. | 554/122 |
| 2003/0181522 A1* | 9/2003 | Strube et al. | 514/558 |
| 2004/0015001 A1* | 1/2004 | Reaney et al. | 554/156 |
| 2004/0225141 A1* | 11/2004 | Rongione et al. | 554/126 |

FOREIGN PATENT DOCUMENTS

| | | |
|---|---|---|
| EP | 0 902 082 | 3/1999 |
| EP | 902082 * | 3/1999 |
| EP | 1 211 304 | 6/2002 |
| WO | WO 97/18320 | 5/1997 |
| WO | WO 2005/014516 | 2/2005 |

OTHER PUBLICATIONS

Yang TS, Liu TT: "Optimization of production of conjugated linoleic acid from soybean oil" J. Agric. Food. Chem., vol. 52, Jul. 14, 2004, pp. 5079-5084.*
Yang, T-S, et al.: "Optimization of Production of Conjugated Linoleic Acid from Soybean Oil", Journal of Agriculture and Food Chemistry, vol. 52, pp. 5079-5084, 2004.

* cited by examiner

*Primary Examiner* — Deborah D Carr
(74) *Attorney, Agent, or Firm* — Morgan Lewis & Bockius LLP

(57) ABSTRACT

A process for the preparation of a material comprising conjugated isomers of a polyunsaturated fatty acid comprises: treating a first fatty acid mixture comprising saturated fatty acids, monounsaturated fatty acids and polyunsaturated fatty acids in the presence of ethanol to form (i) a solid fraction and (ii) a liquid fraction comprising a second fatty acid mixture, wherein the second fatty acid mixture has a higher molar ratio of total polyunsaturated fatty acids to total saturated and monounsaturated fatty acids than the first fatty acid mixture; separating the solid fraction and the liquid fraction; and subjecting the second fatty acid mixture or a derivative or reaction product thereof to treatment with a base in the presence of a solvent, to form conjugated isomers of at least some of the polyunsaturated fatty acids.

18 Claims, No Drawings

PROCESS FOR THE PREPARATION OF FATTY ACIDS

This invention relates to a process for the preparation of a material comprising fatty acids, in particular conjugated isomers of a polyunsaturated fatty acid, to products obtainable by the process and to food products, food supplements or pharmaceutical products comprising the products.

Conjugated isomers of polyunsaturated fatty acids are known to provide health benefits and have been used in food products. Typically, these products comprise linoleic acid isomers with the cis 9, trans 11 and trans 10, cis 12 isomers often being the most abundantly present isomers in these materials, in general in a 1:1 weight ratio.

Conjugated polyunsaturated fatty acids are compounds that contain adjacent carbon-carbon double bonds (eg, one or more —CH═CH—CH═CH— linkages). Conjugated polyunsaturated fatty acids can be prepared from the corresponding non-conjugated fatty acids. For example, EP-A-0902082 describes a process for producing conjugated polyunsaturated fatty acids, such as conjugated linoleic acid (CLA). The process involves subjecting non-conjugated polyunsaturated fatty acids to a treatment with a base in a solvent which is an alcohol with at least 3 carbon atoms and at least two hydroxyl groups.

Typical sources of polyunsaturated fatty acids, such as safflower oil, generally contain about 80% by weight linoleic acid, 12% by weight oleic acid and about 8% by weight saturated fatty acids. Using fractionation and distillation, only the saturated fatty acids can be removed which means that the linoleic acid content cannot exceed 90% by weight. Accordingly, the amount of conjugated linoleic acid that can be produced in a subsequent conjugation step, such as that described above, is also limited to a maximum of 90% by weight.

There is therefore a need for materials that contain high amounts of conjugated polyunsaturated fatty acids.

U.S. Pat. No. 6,395,778 describes a process for making an enriched mixture comprising a non-conjugated polyunsaturated fatty acid ester. The process involves a first step of transesterification of an oil to form fatty acid esters, adding urea to the mixture of fatty acid esters and cooling or concentrating the resulting mixture. The precipitate comprises urea and the saturated fatty acid esters and the liquid fraction contains more of the polyunsaturated fatty acid esters. The specific fatty acid esters disclosed are non-conjugated and contain at least five carbon-carbon double bonds. There is no suggestion that the process can be carried out using free fatty acids.

EP-A-1211304 discloses a method for isolating non-conjugated unsaturated fatty acids by selective crystallisation using urea in methanol as solvent.

There is no disclosure in U.S. Pat. No. 6,395,778 or EP-A-1211304 of subsequent conjugation of the fatty acids.

We have found a process for producing conjugated polyunsaturated fatty acids in surprisingly high yields. Moreover, when carried out on polyunsaturated fatty acids containing two carbon-carbon double bonds, the process results in fewer of the trans, trans isomers of the fatty acids relative to cis, trans isomers. It has been unexpectedly found that the effectiveness of the process is highly dependent on the solvent that is employed in the process.

Accordingly, the present invention provides a process for the preparation of a material comprising a conjugated polyunsaturated fatty acid, which comprises:

treating a first fatty acid mixture comprising saturated fatty acids, monounsaturated fatty acids and non-conjugated polyunsaturated fatty acids in the presence of ethanol to form (i) a solid fraction and (ii) a liquid fraction comprising a second fatty acid mixture, wherein the second fatty acid mixture has a higher molar ratio of total polyunsaturated fatty acids to total saturated and monounsaturated fatty acids than the first fatty acid mixture;

separating the solid fraction and the liquid fraction; and subjecting the second fatty acid mixture or a derivative or reaction product thereof to treatment with a base in the presence of a solvent, to form conjugated isomers of at least some of the polyunsaturated fatty acids.

The process of the invention permits the production of materials containing relatively high amounts of conjugated polyunsaturated fatty acids based on the total amount of fatty acids in the material. Preferably, the material comprises at least 90% by weight, more preferably at least 91%, even more preferably at least 92%, most preferably at least 93%, such as at least 94% or at least 95%, by weight of conjugated polyunsaturated fatty acids based on total fatty acids.

The terms fatty acid, polyunsaturated fatty acids and related terms as used herein refer to straight chain carboxylic acids that contain from 12 to 24 carbon atoms, preferably from 14 to 18 carbon atoms. Saturated fatty acids contain no carbon-carbon double bonds in the alkyl chain, examples are myristic acid (referred to as C14:0), palmitic acid (C16:0) and stearic acid (C18:0). Monounsaturated fatty acids contain one carbon-carbon double bond in the all chain, examples are oleic acid (C18:1) and elaidic acid (C18:1). Polyunsaturated fatty acids contain two or more (preferably two) carbon-carbon double bonds in the allyl chain, examples are linoleic acid (C18:2) and linolenic acid (C18:3).

The process of the invention has been found to be particularly effective when the saturated fatty acids, the monounsaturated fatty acids, and the polyunsaturated fatty acids contain 18 carbon atoms. The conjugated polyunsaturated fatty acids produced from such fatty acids are preferably conjugated linolenic acid (CLA). CLA can exist in a number of isomeric forms, depending on the geometry of the two carbon-carbon double bonds, including: cis 9, trans 11; trans 10, cis 12; cis 9, cis 11; cis 10, cis 12; trans 9, trans 11; and trans 10, trans 12. The cis 9, trans 11 and trans 10, cis 12 isomers are generally the most abundant. The process of the invention can be used to produce any one or all of the isomers, and will generally result in the formation of an isomer mixture in which the cis 9, trans 11 and the trans 10, cis 12 isomers are the predominant CLA isomers.

The process of the invention involves a step of treating a first fatty acid mixture comprising saturated fatty acids, monounsaturated fatty acids and polyunsaturated fatty acids in the presence of ethanol to form (i) a solid fraction and (ii) a liquid fraction comprising a second fatty acid mixture. This treatment provides a liquid fraction having a higher molar ratio of total polyunsaturated fatty acids to total saturated and monounsaturated fatty acids than the first fatty acid mixture. Preferably, this treatment involves treatment with urea, so that the solid fraction comprises urea, typically together with at least a proportion of the saturated fatty acids and/or the monounsaturated fatty acids. The treatment therefore results in a mixture that is enriched in polyunsaturated fatty acids relative to the first fatty acid mixture starting material. It has been surprisingly found that the use of ethanol in this stage of the process, instead of methanol as taught by EP-A-1211304, results in a higher yield of conjugated isomers after the subsequent conjugation step of the invention and, when the polyunsaturated fatty acids contain two carbon-carbon double bonds, a reduction in trans, trans isomers which can be beneficial if cis, trans isomers are required.

In the treatment step, the urea and the first fatty acid mixture are typically combined in liquid form. Preferably, a solution of urea in ethanol is combined with the first fatty acid mixture by adding the solution to the fatty acid mixture or vice versa. The step is generally carried out at a temperature of about 10° C. to 80° C. and is optionally followed by a heating step to increase the temperature to up to 80° C., if necessary. The reaction mixture is then preferably cooled to a temperature at which the urea crystallises from the mixture, such as a temperature of from 0° C. to 30° C. The urea crystals, which contain some saturated fatty acid and/or monounsaturated fatty acid, are separated from the mixture, for example by filtration or centrifugation. The resulting liquid comprises a second fatty acid mixture enriched in polyunsaturated fatty acids.

The amount of urea that is used in the preferred embodiment of the process is preferably sufficient to give a weight ratio of urea:ethanol of at least 1:5, preferably at least 1:4 and more preferably a weight ratio in the range of from 1:4 to 1:2. The amount of urea based on the fist fatty acid mixture is preferably sufficient to give a weight ratio of urea:first fatty acid mixture of at least 2:1, preferably at least 3:1 and more preferably a weight ratio in the range of from 3:1 to 5:1.

The solvent for the process comprises ethanol. The ethanol may contain up to 20% by weight of one or more other solvents such as water and/or methanol. Therefore, the first fatty acid mixture is typically treated in the presence of a solvent comprising at least 80% by weight ethanol.

Preferably, for economic reasons, the ethanol contains from 2% to 10% by weight water.

The second fatty acid mixture that is obtained after treatment of the first fatty acid mixture is optionally subjected to her process steps (prior to treatment with the base in the conjugation step) to form a derivative or reaction product thereof. For example, the further process steps may include purification, removal of solvent from the liquid, esterification to form $C_1$ to $C_6$ alkyl esters of the fatty acids, and combinations of these steps. Generally, any derivatisation or reaction should not have the effect of significantly altering the distribution of fatty acids or, after derivatisation or reaction, fatty acid residues, in the mixture. It is particularly undesirable to reduce the amount of polyunsaturated fatty acids relative to other fatty acids in the mixture.

The first fatty acid mixture may be obtained by methods which are known in the art. The first fatty acid mixture will typically be derived from an animal or vegetable source. The first fatty acid mixture is preferably obtained from an oil comprising from 50% to 85% by weight based on total fatty acids of polyunsaturated fatty acids containing 18 carbon atoms. Suitable vegetable oils include safflower oil, sunflower oil, rape seed oil, cotton seed oil, soybean oil and linseed oil.

The first fatty acid mixture is preferably obtained by a method comprising the hydrolysis of the oil, for example with a base, such as sodium hydroxide. The process may be carried out in the presence of a solvent such as ethanol and is typically followed by acidification to form the fire fatty acids. The free fatty acids may be extracted and optionally purified.

In the process of the invention, the second fatty acid mixture or a derivative or reaction product thereof is subjected to treatment with a base in the presence of a solvent, to form conjugated isomers of at least some of the polyunsaturated fatty acids. The second fatty acid mixture preferably comprises free fatty acids. This process may be carried out according to the teaching in EP-A-0902082, the contents of which are incorporated herein by reference.

The solvent that is used in this step of the process is preferably an alcohol with at least 3 carbon atoms and at least two hydroxyl groups.

A very suitable solvent is 1,3-dihydroxypropane or 1,2-dihydroxyrpropane (ie, propylene glycol). These solvents are foodgrade so that traces left in the products are not harmful. The reaction is preferably performed in the absence of glycerol.

The base that is used in the conjugation step may be any base, but the best results are obtained with NaOH or KOH as base. Suitable concentrations for the base are greater than 0.25 mole/l of solvent, preferably 0.25-3.5 most preferably 1.25-2.75 mole/l. Using higher amounts of base leads to the formation of products, wherein many isomers (in particular C18:2 trans/trans-isomers) are present.

The products are suitably isolated from the crude reaction mixture by the addition of diluted acid to the soap formed until an acidic pH is achieved (preferably: pH 1 to 3), whereupon the oil is separated from the water, washed with water to pH 6 to 8 and dried. The addition of the acid results in the formation of an inorganic salt comprising the cation of the base (such as a sodium ion or potassium ion) and the anion of the acid (such as chloride or sulphate). Thus, the salt formed can be, for example, potassium sulphate. It has been found that the presence of the salt can interfere with subsequent extraction of the product. Therefore, it is preferred that the process comprises the step of removing at least a part of the salt or salts formed from the base and the acid, after the acidification step. The salt may be removed by separation of the salt in solid form from the reaction mixture, when the salt has crystallised or precipitated in the reaction mixture. Preferably, the amount of salt removed is increased by cooling the reaction mixture to increase salt crystallisation or precipitation. Typically, the salt is removed with the aqueous phase by separation of the aqueous phase from the non-aqueous phase, followed by cooling of the non-aqueous phase and removal of the salt thus precipitated or crystallised (e.g., by filtration).

Thus, the invention preferably comprises the step of acidifying the second fatty acid mixture after treatment with the base. The acidified product is optionally purified. It is also preferred that at least a proportion of the salts formed on acidifying is removed and the resulting mixture is subsequently purified. The term "purified" refers to any increase in the content of the conjugated isomers of polyunsaturated isomers in the mixture and does not imply 100% purity. Purification may be effected by removal of any remaining aqueous phase, optionally washing with water and drying, followed by a further process step such as distillation.

The conjugated polyunsaturated fatty acids that are produced in the invention may be subjected to further process steps such as the formation of a mono-, di- or triglyceride of the conjugated isomers of polyunsaturated fatty acids. This step can be carried out using etherification techniques that are well-known in the art.

The product of the invention may be used as a starting material for a process in which the amount of one or more isomers (e.g., geometrical isomers) of the conjugated polyunsaturated fatty acid is enriched relative to the other isomers. A suitable process is described in WO 97/18320. Therefore, the invention contemplates a process for enriching one or more isomers of a conjugated polyunsaturated fatty acid using the product of the invention as a starting material.

In another aspect, the invention provides the use of ethanol as a solvent for the separation of polyunsaturated fatty acids from mixtures containing polyunsaturated fatty acids together with saturated and monounsaturated fatty acids by crystallisation with urea. The esterification process may result in an enrichment in one or more of the isomers, as described in WO 97/18320, the contents of which are incorporated herein by reference.

Also provided by the invention in another aspect is a product obtainable by the process of the invention. It has not previously been possible to produce fatty acid mixtures containing saturated fatty acids, monounsaturated fatty acids and conjugated isomers of polyunsaturated fatty acids, with the conjugated isomers of polyunsaturated fatty acids being present in amounts greater than 90% by weight based on total fatty acids.

Preferably, the product of the invention comprises at least 90% (more preferably at least 92%, such as at least 93% or at least 94%, even more preferably at least 95%) by weight conjugated linoleic acid, at least 43% by weight of the cis-9, trans-11 isomer of conjugated linoleic acid and at least 43% by weight of the trans-10, cis-12 isomer of conjugated linoleic acid, or the same amounts of total mono-, di- and tri-glycerides of these acids, wherein the weight ratio of the cis-9, trans-11 isomer to the trans-10, cis-12 isomer is in the range of 1.1:1 to 1:1.1 (more preferably 1.05:1 to 1:1.05).

All percentages are by weight based on total fatty acids. These products may comprise less than 1.5% by weight (more preferably less than 1.0% by weight, such as less than 0.7% by weight) of trans, trans isomers of conjugated linoleic acid or glycerides thereof. The products may comprise up to 0.2% by weight saturated fatty acids and/or up to 7.5% by weight monounsaturated fatty acids, or glycerides of either fatty acids.

The invention also provides a food product, food supplement or pharmaceutical product comprising a product of the invention.

Products of the invention are optionally used as a blend with a complementary fat.

The blend may comprise 0.3-95 wt %, preferably 2-80 wt %, most preferably 5-40 wt % of the product of the invention and 99.7-5 wt %, preferably 98-20 wt %, most preferably 95-60 wt % of a complementary fat selected from: cocoa butter, cocoa butter equivalents, palm oil or fractions thereof, palmkernel oil or fractions thereof, interesterified mixtures of said fats or fractions thereof, or liquid oils, selected from: sunflower oil, high oleic sunflower oil, soybean oil, rapeseed oil, cottonseed oil, fish oil, safflower oil, high oleic safflower oil, maize oil and MCT-oils.

The food products of the invention (which term includes animal feed), may contain a fat phase, wherein the fat phase contains the product of the invention. The food products are suitably selected from the group consisting of: spreads, margarines, creams, dressings, mayonnaises, ice-creams, bakery products, infant food, chocolate, confectionery, sauces, coatings, cheese and soups.

Food supplements or pharmaceutical products of the invention may be in the form of capsules or other forms, suitable for enteral or parenteral application and comprise a product of the invention.

Examples of suitable food products include those selected from the group consisting of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaises, cheeses, cream alternatives, dry soups, drinks, cereal bars, sauces, snack bars, dairy products, clinical nutrition products and infant formulations.

Pharmaceutical products include pharmaceutical compositions, such as in the form of tablets, pills, capsules, caplets, multiparticulates including: is granules, beads, pellets and micro-encapsulated particles; powders, elixirs, syrups, suspensions and solutions. Pharmaceutical compositions will comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions and syrups. Optionally, the compositions comprise one or more flavoring and/or colouring agents.

Pharmaceutically acceptable carriers suitable for use in such compositions are well known in the art of pharmacy. The compositions of the invention may contain 0.1-99% by weight of conjugated fatty acid. The compositions are generally prepared in unit dosage form. Preferably the unit dosage of conjugated fatty acid is from 1 mg to 1000 mg (more preferably from 100 mg to 750 mg). The excipients used in the preparation of these compositions are the excipients known in the art.

Examples of food supplements include products in the form of a soft gel or a hard capsule comprising an encapsulating material selected from the group consisting of gelatin, starch, modified starch, starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the unit dosage of conjugated fatty acid in the food supplements is from 1 mg to 1000 mg (more preferably from 100 mg to 750 mg).

The following non-limiting examples illustrate the present invention. In the examples and throughout this specification, all percentages are percentages by weight unless otherwise indicated.

EXAMPLES

Example 1

27.3 g NaOH was dissolved in 200 ml 95% ethanol. 100 g of safflower oil was added and the solution was refluxed for 2 h. The resulting mixture was split with sulfuric acid, then extracted 3 times with 900 ml of hexane, the hexane layers were combined and washed with distilled water until the pH was about 7, the organic layer was then evaporated using a rotary evaporator. 270 g urea was dissolved in 1500 ml of 95% ethanol at 30° C. and fatty acids were added, then the mixture was heated to 60° C. for 1 hour and then cooled to 20° C. for 3 hours. The material was filtered to remove the urea crystals and the filtrate was then evaporated. 16.8 g KOH was dissolved in 55 ml propylene glycol in the flask, then 50 g of the fatty acid mixture obtained from the filtrate after evaporation (which contains more than 90% linoleic acid) was added. The flask was flushed with nitrogen at 150° C. for 15 hours. After conjugation, the reaction mixture was placed into hot 10% sulfalic acid solution, the down layer was discarded and the up layer was washed with hot water till pH 7, and finally dried over nitrogen. The conjugated linoleic acid seas analyzed by GC, HPLC and the results are presented in Table 1.

Example 2

Comparative Example

The procedure of Example 1 was repeated using exactly the same conditions except that the reaction with urea was performed with methanol instead of 95% ethanol. After the reaction, the conjugated linoleic acids were analyzed and the results are shown in Table 1.

TABLE 1

FAME (fatty acid methyl ester) analysis

| | Examples | |
|---|---|---|
| | 1 Ethanol | 2 Methanol |
| C14:0 | 0.0 | 0.0 |
| C16:0 | 0.1 | 0.3 |
| C16:1c | 0.1 | 0.1 |
| C18:0 | 0.0 | 0.0 |
| C18:1 c | 6.9 | 8.6 |
| C18:2 c,c | 0.4 | 0.4 |
| C18:3 c,c,c | 0.1 | 0.2 |
| CLA-9,11 c,c | 1.0 | 1.1 |
| CLA-10,12 c,c | 1.1 | 1.1 |
| CLA-11,13 c,c | 1.3 | 1.0 |
| CLA-OX | 0.0 | 0.3 |
| C18:2 t,t | 1.1 | 1.3 |
| CLA-t,t | 1.2 | 2.0 |
| CLA-9,11 c,t | 43.0 | 41.6 |
| CLA-10,12 t,c | 43.3 | 42.1 |
| SAFA | 0.1 | 0.4 |
| main CLA | 86.3 | 83.7 |
| total CLA | 91.2 | 89.1 |

Cx:y refers to fatty acids containing x carbon atoms and y double bonds
c means cis and t means trans
CLA is conjugated linoleic acid; CLA-OX refers to CLA oxidation products
in CLA m,n, m and n are the positions of the double bonds in the chain e.g., CLA-9,11 refers to the 9,11-dienoic acid
SAFA means saturated fatty acids The table shows the advantages of the process of the invention using ethanol instead of methanol ie, there is a higher amount of total CLA and main CLA isomers, less trans, trans isomers.

Example 3

Spreads containing triglycerides of the product of Example 1 can be formulated as follows, using the method described in WO 97/18320.

| | wt % |
|---|---|
| Fat Phase | |
| Fat Blend* | 40 |
| Hymono 7804 | 0.3 |
| Colour (2% β-carotene) | 0.02 |
| Total | 40.32 |
| Aqueous Phase (to pH 5.1) | |
| Water | 56.44 |
| Skimmed Milk Powder | 1.5 |
| Gelatin (270 bloom) | 1.5 |
| Potassium Sorbate | 0.15 |
| Citric Acid Powder | 0.07 |
| Total | 59.66 |

*Blend of hardstock/Sunflower oil/glycerides of the product of Example 1 (13/82/5 by weight)

Example 4

Dressings containing glycerides of the product of Example 1 can be formulated as follows, using the method described in WO 97/18320.

| | wt % |
|---|---|
| Liquid oil* | 25.0 |
| Maltodextrin | 20.0 |
| Dried egg yolk | 0.8 |
| Xanthum gum | 0.4 |
| Vinegar | 5.0 |
| Water | 48.8 |

*Interesterified mixture of the product with sunflower oil

Example 5

This example relates to the conjugation of enriched safflower oil on pilot plant scale.

60 kg of potassium hydroxide (50% (wt) solution, KOH) was mixed with 115 kg of propylene glycol. This mixture was heated to 70° C., while nitrogen was bubbled through the mixture. After this, the nitrogen bubbling was stopped and 95 kg of enriched safflower fatty acids prepared using urea according to the present invention were added to the alkali propylene glycol.

The temperature was then increased to 110° C., and the mixture was stilled at this temperature for 2 hours. After this, the temperature was increased to 135° C. and the mixture was stirred at this temperature until the C18:2c content was below 1%. This was monitored by removing samples at regular time intervals and analyzing the FAME composition by GC. In total, three batches were carried out and the average total reaction time was 82 hours.

The soap from each batch was split with concentrated sulphuric acid. After the conjugation reaction, the mixture was cooled down to 70° C. and diluted with 250 L of hot demi-water. After this, 30 kg of concentrated sulphuric acid was added to split the soap.

The obtained mixture was settled and the bottom layer was drained.

The oil-phases from the three batches were put together and were washed with hot demi-water at 80° C. After first washing an emulsion layer was is formed and therefore only a part of the added water could be drained. During the second washing the emulsion remains and after draining a part of the added water the oil was dried by applying vacuum.

The dried oil was distilled over short path distillation. The yield is 170 kg. Because of the emulsion there was a loss (about 40%) of product yield.

The FAME analysis of the product in given in Table 2 below.

TABLE 2

| | End mixture | end product |
|---|---|---|
| C14:0 | 0 | 0 |
| C16:0 | 0.2 | 0.2 |
| C16:1c | 0.1 | 0.1 |
| C18:0 | 0 | 0 |
| CLA t,t | 0.9 | 1.4 |
| CLA c9,c11 | 0.9 | 1 |
| CLA c10,c12 | 0.9 | 1 |
| CLA 11,13 | 1 | 0.8 |
| C18:1t | 0 | 0 |

TABLE 2-continued

|  | End mixture | end product |
|---|---|---|
| C18:1c | 4.9 | 4.7 |
| CLA_OX | 0.1 | 0.2 |
| C18:2 t,t | 0.6 | 0.4 |
| C18:2 c,c | 0.9 | 1.3 |
| C20:0 | 0 | 0 |
| C20:1c | 0 | 0 |
| SAFA | 0.3 | 0.2 |
| Main CLA | 89.4 | 88.8 |
| CLA c9,t11 | 44 | 43.3 |
| CLA t10,c12 | 45.5 | 45.5 |
| Total CLA | 93.2 | 93.2 |

Example 6

7700 kilograms of enriched safflower fatty acids were added to 9780 kilograms of propylene glycol under nitrogen blanketing in a stirred tank reactor. To this, 5120 kilograms of potassium hydroxide (50 wt-% solution, KOH) was added and heated to 110° C. under nitrogen. After removal of the water, the temperature was increased to 139° C. and stirred at this temperature until the C18:2cis content in the FAME-analysis was below 1%. The total reaction time was 42 hours.

After conjugation, the mixtures was first cooled to 100° C. and then diluted with 25 tons of demi-water, followed by cooling to 55° C. The diluted soap was split with 3090 kg of concentrated sulphuric acid (98 wt %). The fatty acid mixture was settled and the bottom water layer was drained. Potassium sulphate crystals, formed during splitting, were removed completely with the water phase during draining of the bottom layer. The remaining fatty acid phase was cooled to 55° C. to crystallize all remaining potassium sulphate. This was also removed to prevent emulsion formation in the following steps.

The fatty acids phase was heated to 95° C. and washed in two steps with respectively 10 tons and 5 tons of hot demi-water (95° C.). No emulsion was found in the washing steps. After washing the oil was dried for distillation.

The washed fatty acids was distilled by short path distillation to yield 6200 kg of product. Yield loss was reduced to 20%.

The FAME analysis of the product is shown below in Table 3.

TABLE 3

|  | Product analysis |
|---|---|
| C14:0 | 0.0 |
| C16:0 | 0.2 |
| C16:1c | 0.1 |
| C18:0 | 0.1 |
| CLA t,t | 0.9 |
| CLA c9,c11 | 0.9 |
| CLA c10,c12 | 0.9 |
| CLA 11,13 | 0.8 |
| C18:1t | 0.0 |
| C18:1c | 4.8 |
| CLA_OX | 0.2 |
| C18:2 t,t | 0.6 |
| C18:2 c,c | 0.6 |
| C20:0 | 0.0 |
| C20:1c | 0.0 |
| SAFA | 0.4 |
| Main CLA | 89.9 |
| CLA c9,t11 | 44.3 |
| CLA t10,c12 | 45.6 |
| Total CLA | 93.6 |

The invention claimed is:

1. Process for the preparation of a material comprising conjugated isomers of a polyunsaturated fatty acid, which comprises:
   treating a first fatty acid mixture, comprising saturated fatty acids, monounsaturated fatty acids and polyunsaturated fatty acids in the presence of ethanol to form (i) a solid fraction and (ii) a liquid fraction comprising a second fatty acid mixture, wherein the second fatty acid mixture has a higher molar ratio of total polyunsaturated fatty acids to total saturated and monounsaturated fatty acids than the first fatty acid mixture;
   separating the solid fraction and the liquid fraction; and
   subjecting the second fatty acid mixture or a derivative or reaction product thereof to treatment with a base in the presence of a solvent, to form conjugated isomers of at least some of the polyunsaturated fatty acids.

2. Process as claimed in claim 1, wherein the material comprises at least 90% by weight of conjugated isomers of polyunsaturated fatty acids.

3. Process as claimed in claim 1 or claim 2, wherein the polyunsaturated fatty acids contain from 12 to 24 carbon atoms.

4. Process as claimed in claim 1, wherein the saturated fatty acids, the monounsaturated fatty acids, and the polyunsaturated fatty acids contain 18 carbon atoms.

5. Process as claimed in claim 1, wherein the conjugated isomers are conjugated isomers of linoleic acids.

6. Process as claimed in claim 1, wherein the first fatty acid fraction is treated with urea and the solid fraction comprises urea.

7. Process as claimed in claim 1, wherein the first fatty acid mixture is treated in the presence of a solvent comprising at least 80% by weight ethanol.

8. Process as claimed in claim 1, wherein the second fatty acid mixture is subjected to further process steps prior to treatment with the base to form a derivative or reaction product thereof.

9. Process as claimed in claim 8, wherein the further steps are selected from purification, removal of solvent, esterification to form $C_1$ to $C_6$ alkyl esters of the fatty acids and combinations thereof.

10. Process as claimed in claim 1, wherein the first fatty acid mixture is obtained from an oil comprising from 50% to 85% by weight based on total fatty acids of fatty acids containing 18 carbon atoms.

11. Process as claimed in claim 1, wherein the first fatty acid mixture is obtained by a method comprising the hydrolysis of vegetable oil with a base in the presence of ethanol as solvent.

12. Process as claimed in claim 11, wherein the vegetable oil is selected from the group consisting of safflower oil, sunflower oil, rape seed oil, cotton seed oil, soybean oil and linseed oil.

13. Process as claimed in claim 1, wherein the solvent comprises an alcohol having three carbon atoms and at least two hydroxyl groups.

14. Process as claimed in claim 1, wherein the solvent is propylene glycol.

15. Process as claimed in claim 1, which comprises acidifying the second first fatty acid mixture after treatment with a base.

16. Process as claimed in claim 15, wherein at least a proportion of the salts formed on acidifying is removed and the resulting mixture is subsequently purified.

17. Process as claimed in claim 1, further comprising the step of forming a mono-, di- or triglyceride of the conjugated isomers polyunsaturated fatty acids.

18. The method for the separation of polyunsaturated fatty acids from mixtures containing polyunsaturated fatty acids together with saturated and monounsaturated fatty acids which comprises crystallisation with urea in the presence of ethanol as a solvent.

* * * * *